(12) United States Patent
Sakyu et al.

(10) Patent No.: US 8,664,457 B2
(45) Date of Patent: Mar. 4, 2014

(54) METHOD FOR PRODUCING 3,3,3-TRIFLUOROPROPENE

(75) Inventors: Fuyuhiko Sakyu, Saitama (JP); Yasuo Hibino, Shiki (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/576,600

(22) PCT Filed: Jan. 18, 2011

(86) PCT No.: PCT/JP2011/050688
§ 371 (c)(1),
(2), (4) Date: Aug. 1, 2012

(87) PCT Pub. No.: WO2011/102167
PCT Pub. Date: Aug. 25, 2011

(65) Prior Publication Data
US 2012/0302804 A1    Nov. 29, 2012

(30) Foreign Application Priority Data
Feb. 16, 2010   (JP) ................................. 2010-031867

(51) Int. Cl.
*C07C 21/18*    (2006.01)
(52) U.S. Cl.
USPC ........................... 570/158; 570/156; 570/169
(58) Field of Classification Search
None
See application file for complete search history.

(56) References Cited

U.S. PATENT DOCUMENTS

| 4,465,786 | A | 8/1984 | Zimmer et al. | |
| 4,798,818 | A | 1/1989 | Baizer et al. | |
| 6,958,424 | B1 * | 10/2005 | Nair et al. | 570/261 |
| 2007/0123741 | A1 | 5/2007 | Van Der Puy et al. | |
| 2008/0300432 | A1 * | 12/2008 | Hedrick et al. | 570/158 |

FOREIGN PATENT DOCUMENTS

| EP | 0 396 974 A1 | 11/1990 |
| JP | 59-80332 A | 5/1984 |
| JP | 59-108726 A | 6/1984 |
| JP | 1-168347 A | 7/1989 |
| JP | 2-286635 A | 11/1990 |
| JP | 9-194404 A | 7/1997 |
| JP | 10-67693 A | 3/1998 |
| JP | 2008-162999 A | 7/2008 |
| JP | 2011-42646 A | 3/2011 |

OTHER PUBLICATIONS

Masesane, I. B. et. al. Palladium-Catalysed transfer hydrogenation of alkenes in the presence of Zinc Powder and various organic acids, Bull. Chem. Soc. Ethiop. 2005, 19, 149-152.*
Ohnishi, R. et. al. Bi-Pd Catalyst for selective hydrochlorination of 1,1,2-trichlorotrifluoroethane to trifluoroethene, a key intermediate to 1,1,1,2-tetrafluoroethane as a CFC replacement for refrigeration, Chem. Lett. 1991, 5, 841-844.*
Masesane, I. B. et al. Bull. Chem. Soc. Ethiop. 2005, 19, 149-152.*
Ohnishi, R. et al., Chem. Lett. 1991, 5, 841-844.*
Ma, Z. et al. Ency. Inorg. Chem. 2006, 1-17.*
International Search Report with English translation dated Apr. 12, 2011 (three (3) sheets).
Form PCT/ISA/237 (three (3) sheets).
Gable et al., "Efficient Catalytic Deoxygenation of Epoxides Using [Tris(3,5-dimethylpyrazolyl) hydridoborato] rhenium Oxides", Organometallics, 2000, vol. 19, pp. 944-946 (three (3) sheets).
English Translation of I. L. Knunyants et al., "Catalytic Hydrogenation of Perfluoro Olefins", Reactions of Fluoro Olefins, Communication 13., 1960, pp. 1312-1317.
Extended European Search Report dated Aug. 2, 2013 (seven (7) pages).

* cited by examiner

*Primary Examiner* — Johann R Richter
*Assistant Examiner* — Medhanit Bahta
(74) *Attorney, Agent, or Firm* — Crowell & Moring LLP

(57) ABSTRACT

A production method of 3,3,3-trifluoropropene includes the step of hydrogenating 1-chloro-3,3,3-trifluoropropene with hydrogen ($H_2$) in a gas phase in the presence of either of: (A) a catalyst having carried on a carrier at least one kind of transition metal selected from the group consisting of ruthenium, nickel, rhodium, iridium, iron, osmium and cobalt, or an oxide of said transition metal; (B) an oxide catalyst of copper and manganese; and (C) a catalyst having carried on a carrier palladium and at least one kind of element selected from the group consisting of bismuth, zinc, copper, silver, lanthanum, lead, zirconium, niobium, hafnium, magnesium, tin and arsenic.

7 Claims, No Drawings

METHOD FOR PRODUCING 3,3,3-TRIFLUOROPROPENE

TECHNICAL FIELD

The present invention relates to a method for producing 3,3,3-trifluoropropene, which is usable as a functional material or biologically active material, such as a cooling medium, a blowing agent, a cleaning agent, a solvent, an etching agent or an aerosol, an intermediate of a functional material, or a monomer of a polymer compound.

BACKGROUND ART

There have been a large number of researches made on 3,3,3-trifluoropropene, which is the target compound of the present invention, and derivatives thereof.

For example, Patent Document 1 discloses a method of producing 3,3,3-trifluoropropene by fluorination of 1,1,1,3-tetrachloropropane with hydrogen fluoride in gas phase in the presence of a chromium fluoride-carrying activated alumina catalyst and/or a phosphoric acid-carrying alkaline-earth metal catalyst, wherein, during or after the fluorination, oxygen or oxygen-containing gas is added in an amount of 5 to 30 mol % based on the total supply amount of the raw material.

Patent Document 2 discloses a method of producing 3,3,3-trifluoropropene by reacting 1,1,1,3-tetrahalopropane with a theoretically excessive amount of anhydrous hydrogen fluoride in gas phase at a temperature of about 200° C. or higher through the use of a compound of a transition metal such as cobalt, chromium or iron.

Similarly to Patent Document 2, Patent Document 3 discloses a method of producing 3,3,3-trifluoropropene by fluorinating a halogenated hydrocarbon in gas phase in the presence of a chromium oxyfluoride catalyst.

On the other hand, Patent Document 4 discloses a method of producing 3,3,3-trifluoropropene by providing 1,2-dichloro-3,3,3-trifluoropropene as a starting material, converting the 1,2-dichloro-3,3,3-trifluoropropene to 1-chloro-3,3,3-trifluoropropene, and then, hydrogenating the 1-chloro-3,3,3-trifluoropropene by coexistence with ammonium formate etc. in the presence of a palladium catalyst.

Non-Patent Document 1 discloses a method of producing 3,3,3-trifluoropropene by thermal decomposition of trifluoromethoxysilane.

PRIOR ART DOCUMENTS

Patent Documents

Patent Document 1: Japanese Laid-Open Patent Publication No. S59-108726
Patent Document 2: Japanese Laid-Open Patent Publication No. H1-168347
Patent Document 3: Japanese Laid-Open Patent Publication No. S59-080332
Patent Document 4: U.S. Pat. No. 6,958,424

Non-Patent Documents

Non-Patent Document 1: P. G. Kevin et al., Organometallics, Vol. 19, P. 944-946, 2000

SUMMARY OF THE INVENTION

Problems to be Solved by the Invention

The reduction (reductive dehalogenation) of halogenated olefins by hydrogenation etc. is well-known from many documents. It is however very difficult to find out the reaction conditions for selectively converting (that is, reducing) a halogen atom bonded to an olefin moiety (double-bond moiety) of a halogenated olefin to hydrogen. The reduction of such a halogenated olefin often leads to an unexpected result in the case where a strong electrophilic trifluoromethyl substituent group is bonded to the olefin moiety of the halogenated olefin.

There are known some conventional techniques for reducing a compound having a halogen atom bonded to an olefin moiety with the use of hydrogen. For example, it is known from the following non-patent document that a fluorinated alkane is produced by hydrogenation of a fluorinated olefin with hydrogen in the presence of a palladium catalyst.

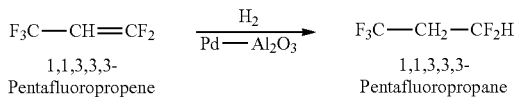

1,1,3,3,3-Pentafluoropropene → 1,1,3,3,3-Pentafluoropropane

Izvest. Akad. Nauk, S.S.S.R., Otdel. Khim. Nauk, 1960, 1412-18: CA55, 349f

There is also known, from the following patent document, a production process of a fluorinated propane as a technique of producing a fluorinated alkane by reacting a fluorinated olefin as a starting material with a reducing agent such as hydrogen gas. More specifically, it is disclosed that hexafluoropropane is produced at a conversion rate of 88.6 to 93.2% by reduction of hexafluoropropene with hydrogen through the use of a palladium-carrying activated carbon (Pd/C) as a catalyst.

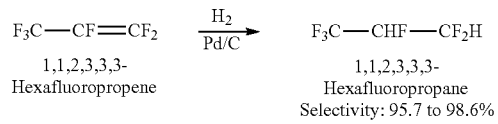

1,1,2,3,3,3-Hexafluoropropene → 1,1,2,3,3,3-Hexafluoropropane
Selectivity: 95.7 to 98.6%

Japanese Laid-Open Patent Publication No. 2008-162999

As mentioned above, it is difficult to obtain a target halogenated olefin efficiently by reaction of a halogenated olefin with hydrogen due to preferential generation of a halogenated propane. In fact, the present inventors reached a result that: when 1-chloro-3,3,3-trifluoropropene, that is, the starting material of the present invention was reacted with hydrogen in the presence of a platinum-, rhenium- or palladium-carrying activated carbon catalyst (Pt/C, Re/C or Pd/C), 3,3,3-trifluoropropane was generated with high selectivity whereby the target 3,3,3-trifluoropropene was hardly produced and isolated (see the after-mentioned comparative example).

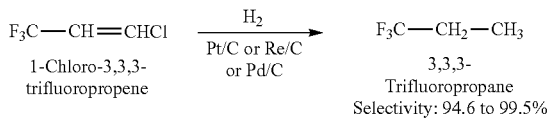

1-Chloro-3,3,3-trifluoropropene → 3,3,3-Trifluoropropane
Selectivity: 94.6 to 99.5%

It has accordingly been considered that it is very difficult to obtain a target product with high selectivity and high yield from a compound having a halogen atom bonded to an olefin moiety by selectively converting only the halogen atom to hydrogen.

For this reason, the conventional techniques often utilize halogenated saturated carbons in place of halogenated olefins as a starting material for production of 3,3,3-trifluoropropene as in the case of Patent Documents 1 to 3. The methods of Patent Documents 1 to 3 are favorable. However, these methods have the safety problem in that each of the methods generally requires a high reaction temperature and needs to use dangerous-to-handle hydrogen fluoride. These methods also have the problems to be improved, such that the generation of by-products including fluorinated propane e.g. 1,1,1,3,3-pentafluoropropane and 1-chloro-3,3,3-trifluoropropene makes it difficult to separate and purify the target 3,3,3-trifluoropropene and causes increase in equipment load. Thus, the methods of Patent Documents 1 to 3 are not always favorable.

Further, the method of Patent Document 4 cannot be said to be effective for industrial production by continuous reaction process due to the use of expensive palladium catalyst, the need for coexistence of a formate salt such as ammonium formate in the reaction system and the progress of the reaction in liquid phase.

The method of Non-Patent Publication 1 is useful as the target 3,3,3-trifluoropropene can be obtained only by thermal decomposition. However, both of trifluoromethoxysilane as a starting material and a rhenium catalyst are expensive. The method of Non-Patent Publication 1 is thus difficult to adopt for industrial production.

As mentioned above, the conventional techniques are not always satisfactory as industrial production methods for mass production of 3,3,3-trifluoropropene, that is, the target compound of the present invention. There has been a demand to establish an industrially easily practicable production method of 3,3,3-trifluoropropene.

Means for Solving the Problems

It is therefore an object of the present invention to provide an industrially easily practicable production method of 3,3,3-trifluoropropene.

As a result of extensive researches, the present inventors have found that, when 1-chloro-3,3,3-trifluoropropene is hydrogenated with hydrogen ($H_2$) in gas phase in the presence of either of "(A) a catalyst having, carried on a carrier, at least one kind of transition metal selected from the group consisting of ruthenium, nickel, rhodium, iridium, iron, osmium and cobalt, or an oxide of the transition metal", "(B) an oxide catalyst of copper and manganese" and "(C) a catalyst having, carried on a carrier palladium, and at least one kind of element selected from the group consisting of bismuth, zinc, copper, silver, lanthanum, lead, zirconium, niobium, hafnium, magnesium, tin and arsenic", the selective reduction of a halogen atom boned to an olefin moiety of the 1-chloro-3,3,3-trifluoropropene proceeds preferentially so as to allow high-selectivity production of 3,3,3-trifluoropropene with almost no 3,3,3-trifluoropropane by-product. This reaction process is very easy and practically advantageous for industrial-scale production of 3,3,3-trifluoropropene. The present inventors have also found preferable criteria for obtaining the target compound with higher selectivity by controlling the reaction conditions such as mol ratio during the hydrogenation. The present invention is based on these findings.

Namely, the present invention provides a method for producing 3,3,3-trifluoropropene as defined in the following inventive aspects.

[Inventive Aspect 1]

A method for producing 3,3,3-trifluoropropene, comprising: performing hydrogenation of 1-chloro-3,3,3-trifluoropropene with hydrogen ($H_2$) in gas phase in the presence of either of "(A) a catalyst having, carried on a carrier, at least one kind of transition metal selected from the group consisting of ruthenium, nickel, rhodium, iridium, iron, osmium and cobalt, or an oxide of the transition metal", "(B) an oxide catalyst of copper and manganese" and "(C) a catalyst having, carried on a carrier, palladium and at least one kind of element selected from the group consisting of bismuth, zinc, copper, silver, lanthanum, lead, zirconium, niobium, hafnium, magnesium, tin and arsenic".

[Inventive Aspect 2]

The method for producing 3,3,3-trifluoropropene according to Inventive Aspect 1, wherein the amount of the transition metal carried is 0.1 to 20 mass % based on the amount of the carrier.

[Inventive Aspect 3]

The method for producing 3,3,3-trifluoropropene according to Inventive Aspect 1 or 2, wherein the hydrogenation is performed at a temperature of 150 to 300° C.

[Inventive Aspect 4]

The method for producing 3,3,3-trifluoropropene according to any one of Inventive Aspects 1 to 3, wherein the amount of the hydrogen is 1 to 5 mol per 1 mol of the 1-chloro-3,3,3-trifluoropropene.

[Inventive Aspect 5]

The method for producing 3,3,3-trifluoropropene according to Inventive Aspect 1, further comprising: recovering and returning unreacted 1-chloro-3,3,3-trifluoropropene to the reaction system.

The target 3,3,3-trifluoropropene has a relatively low boiling point and thus, when mixed with non-condensable hydrogen or hydrogen chloride, mainly exists as a gas under room temperature and atmospheric pressure (0.1 MPa). When the crude product containing the 3,3,3-trifluoropropene is generated in a flow gas-phase reactor or pressure-resistance reaction vessel, it is feasible to extract the crude product by flowing the crude product through a condenser cooled to lower than 0° C. and, more specifically, a temperature lower than or equal to the boiling point, removing excessive hydrogen or hydrogen chloride etc. and condensing the gas product. It is further feasible to purify the crude product by washing away a trace amount of acid with water from the crude product, and then, subjecting the crude product to distillation separation.

In this way, it is possible according to the present invention that the target 3,3,3-trifluoropropene can be produced with higher yield and higher productivity than conventional techniques under industrially easily practicable production conditions with no environmental load.

DETAILED DESCRIPTION OF THE EMBODIMENTS

Hereinafter, the present invention will be described below in detail.

In the present invention, 3,3,3-trifluoropropene is produced by hydrogenation of 1-chloro-3,3,3-trifluoropropene with hydrogen ($H_2$) in the presence of either of "(A) a catalyst having, carried on a carrier, at least one kind of transition metal selected from the group consisting of ruthenium, nickel, rhodium, iridium, iron, osmium and cobalt, or an oxide of the transition metal", "(B) an oxide catalyst of copper and manganese" and "(C) a catalyst having, carried on a carrier, palladium and at least one kind of element selected from the group consisting of bismuth, zinc, copper, silver, lanthanum, lead, zirconium, niobium, hafnium, magnesium, tin and arsenic" (hereinafter referred to as "catalyst A", "catalyst B" and "catalyst C", respectively, throughout the specification).

There is no particular limitation on the 1-chloro-3,3,3-trifluoropropene used as the starting material in the present invention. For example, it is feasible to obtain the 1-chloro-3,3,3-trifluoropropene by a process disclosed in Japanese Laid-Open Patent Publication No. H9-194404 or No. H10-067693. The 1-chloro-3,3,3-trifluoropropene can be obtained as a trans isomer (E isomer) and a cis isomer (Z isomer). In the present invention, the trans and cis isomers can be used alone or in the form of a mixture thereof without particular limitation.

In the catalyst A, ruthenium, nickel, rhodium and iridium are preferred as the transition metal.

In the case where the catalyst A is in the form of having the transition metal carried on the carrier, there can be used alumina, fluorinated alumina, fluorinated aluminium, activated carbon, zirconia, fluorinated calcium, silica or the like as the carrier.

There can also be used alumina, fluorinated alumina, fluorinated aluminium, activated carbon, zirconia, fluorinated calcium, silica or the like as the carrier in the catalyst C.

Examples of the activated carbon used as the carrier are plant-based activated carbons prepared using wood, wood charcoal, coconut shell charcoal, palm shell charcoal, raw ash etc. as raw materials; coal-based activated carbons prepared using peat coal, lignite, brown coal, bituminous coal, anthracite etc. as raw materials; petroleum-based activated carbons prepared using petroleum pitch, oil carbon etc. as raw materials; and synthetic resin-based activated carbons prepared using polyvinylidene chloride etc. as raw materials. These activated carbons are commercially available and usable. For example, there can be used bituminous coal activated carbon (granular activated carbon available under the trade name of BPL from Toyo Calgon Co., Ltd.), coconut shell activated carbon (available under the trade name of Granular Shirasagi GX, G2X, SX, CX or XRC from Japan EnviroChemicals Ltd. or available under the trade name of PCB from Toyo Calgon Co., Ltd.). The activated carbon is not however limited to the above examples. In general, the activated carbon is used in the form of particles. The shape and size of the activated carbon can be selected as appropriate based on the general knowledge of those skilled in the art as long as the activated carbon is adaptable to the reactor. The activated carbon can be in various forms such as spherical form, fibrous foam, powder form and honeycomb form. Preferably, the activated carbon used has a large specific surface in the present invention. The specific surface and pore volume of the activated carbon can be within the specifications of commercially available activated carbons. It is particularly preferable that the activated carbon has a specific surface of larger than 400 $m^2/g$ and a pore volume of larger than 0.1 $cm^3/g$, more preferably a specific surface of 800 to 3000 $m^2/g$ and a pore volume of 0.2 to 1.0 $cm^3/g$. It is further preferable, in the case of using the activated carbon as the catalyst carrier, to activate a surface of the carrier and remove an ash content from the surface of the carrier by immersing the carrier in an aqueous basic solution of ammonium hydroxide, sodium hydroxide, potassium hydroxide etc. for about 10 hours or more at around room temperature or by pretreating the carrier with an acid such as nitric acid, hydrochloric acid or hydrofluoric acid as is commonly done.

Specific examples of the catalyst having the transition metal carried on the carrier as the catalyst A include: ruthenium/activated carbon (Ru/C); nickel/activated carbon (Ni/C); rhodium/activated carbon (Rh/C); and iridium/activated carbon (Ir/C).

Specific examples of the catalyst C include: palladium-bismuth/activated carbon (Pd—Bi/C); palladium-bismuth/alumina (Pd—Bi/$Al_2O_3$); palladium-bismuth/zirconia (Pd—Bi/$ZrO_2$); palladium-lead/activated carbon (Pd—Pb/C); palladium-lead/alumina (Pd—Pb/$Al_2O_3$); and palladium-lead/zirconia (Pd—Pb/$ZrO_2$).

There is no particular limitation on the process for preparation of the catalyst having the transition metal carried on the carrier as the catalyst A.

There is also no particular limitation on the process for preparation of the catalyst C.

For example, it is feasible to prepare the catalyst by providing a solution in which a soluble compound of the metal to be carried is dissolved, impregnating the carrier with the solution or spraying the solution onto the carrier, drying the solution-applied carrier, and then, bringing the resulting metal salt-carrying carrier into contact with hydrogen fluoride, hydrogen chloride, chlorofluorohydrocarbon etc. under heating conditions for halogen modification of part or the whole of the carried metal or the carrier. The soluble compound of the metal to be carried can be either a nitrate, a chloride, an oxychloride or an oxide of the metal, which is soluble in a solvent such as water, methanol, ethanol or acetone. Further, there may be used any process for fluorination of the carrier. For example, the fluorinated alumina can be prepared from a commercially available alumina for drying or for use as a catalyst carrier by flowing hydrogen fluoride through the alumina in gas phase under heating, or by spraying an aqueous solution of hydrogen fluoride onto the alumina or immersing the alumina in an aqueous solution of hydrogen fluoride at around room temperature, and then, drying the alumina.

In each of the catalyst A and the catalyst C, the amount of the metal carried is generally 0.05 to 40 mass %, preferably 0.1 to 20 mass %, based on the amount of the carrier. In the case where two or more kinds of transition metals are carried on the carrier, it is preferable to control the amount of the transition metal used as the main component to be within the above-mentioned range.

In the catalyst C, the amount of the additive element is generally 5 to 75 mass %, preferably 10 to 50 mass %, based on the total amount of the palladium and the additive element.

On the other hand, specific examples of the catalyst B include a catalyst containing oxides of copper and manganese as the main components as indicated in the after-mentioned example, that is, "a catalyst predominantly composed of copper (II) oxide and manganese (IV) oxide". The content ratio of the copper (II) oxide and manganese (IV) oxide in the catalyst B is generally copper (II) oxide:manganese (IV) oxide=1:0.3 to 6.0, preferably 1:0.5 to 5.0, in terms of mass ratio. In addition to the above oxides, any other metal oxide or oxides such as chromium oxide, magnesium oxide, aluminum oxide, cobalt oxide and silver oxide may also be contained. In such a case, the amount of the copper (II) oxide and manganese (IV) oxide is 60 mass % or more, preferably 70 mass % or more, based on the total amount of the catalyst. This catalyst can be prepared by a person skilled in the art with reference to any known process or can be commercially available.

In general, it suffices to use the hydrogen ($H_2$) in a stoichiometric amount, i.e., in an amount of 1 mol per 1 mol of the 1-chloro-3,3,3-trifluoropropene. The amount of the hydrogen used is preferably 2 to 30 mol per 1 mol of the 1-chloro-3,3,3-trifluoropropene. When the reaction is performed in a flow system, it suffices to control the pressure of the hydrogen reaction to be higher than or equal to atmospheric pressure. In order to perform the desired reaction efficiently, the hydrogen pressure is preferably 0.1 to 50 MPa (with reference to absolute pressure, the same applies to the following). The hydrogen pressure is particularly preferably 0.1 to 2.0 MPa in view of the practicality. When the reaction is performed in a batch system, it is preferable to control the pressure of the hydrogen to be higher than atmospheric pressure. The hydrogen pressure is preferably 0.2 to 10 MPa. In view of the practicality, the hydrogen pressure is particularly preferably 0.5 to 5.0 MPa. In the batch system, it is preferable to allow coexistence of a base such as sodium hydroxide as an acid acceptor in view of the generation of hydrogen chloride.

When the reaction is performed in a flow system, the contact time is generally 0.1 to 300 seconds, preferably 1 to 60 seconds. When the reaction is performed in a batch system, the reaction time is no particularly limited and is generally 72 hours or less. As the reaction time varies depending on the catalyst, the reaction substrate and the reaction conditions, it is preferable to determine the time at which the raw material has almost disappeared as the end of the reaction while monitoring the progress of the reaction by any analytical means such as gas chromatography, thin-layer chromatography, liquid chromatography or nuclear magnetic resonance.

In the present invention, a solvent may be added separately. There is no particular limitation on the solvent as long as the solvent is not involved in the reaction. Examples of the solvent are: water; aliphatic hydrocarbons such as n-hexane, cyclohexane and n-heptane; aromatic hydrocarbons such as benzene, toluene, α,α,α-trifluorotoluene, xylene, ethylbenzene and mesitylene; halogenated hydrocarbons such as methylene chloride, chloroform and 1,2-dichloroethane; and ethers such as diethyl ether, 1,2-dimethoxyethane, 1,4-dioxane, tetrahydrofuran, 2-methyltetrahydrofuran, t-butyl methyl ether, diisopropyl ether, diethylene glycol dimethyl ether and anisole. Among others, n-hexane, n-heptane, toluene, xylene, diethyl ether, 1,4-dioxane and tetrahydrofuran are preferred. Particularly preferred are n-hexane, toluene, diethyl ether and tetrahydrofuran. These solvents can be used alone or in combination of two or more kinds thereof.

There is no particular limitation on the reaction pressure. The reaction can be performed under normal atmospheric pressure conditions or pressurized conditions. The reaction pressure is generally 0.1 to 2 MPa, preferably 0.1 to 0.5 MPa.

Further, there is no particular limitation on the reaction temperature. The reaction temperature is generally 50 to 600° C., preferably 100 to 350° C. If the reaction pressure is lower than 50° C., the reaction is slow and is not practical. If the reaction temperature exceeds 600° C., the life of the catalyst becomes short so that the reaction proceeds rapidly but may result in a deterioration in the selectivity of the 3,3,3-trifluoropropene due to generation of a decomposition product.

In the present invention, the reaction can be performed in the reactor under normal atmospheric pressure conditions or pressurized conditions. When the reaction is performed under pressurized conditions, there is no particular limitation on the material of the reactor as long as the reactor is capable of withstanding such pressurized conditions. As the reactor, there can be used reactor with a lining of tetrafluoroethylene resin, chlorotrifluoroethylene resin, vinylidene fluoride resin, PFA resin, glass etc. or a reaction vessel of glass. Although a reaction vessel having an inner wall of stainless steel, iron etc. is usable, such a metal material could be subjected to corrosion by hydrogen chloride gas generated during the progress of the reaction in the present invention. It is thus preferable to use a corrosion-resistant metal material such as Monel, Inconel or Hastelloy.

The 3,3,3-trifluoropropene obtained by the method of the present invention exists as a gas under room temperature and atmospheric pressure. It is thus feasible to obtain the 3,3,3-trifluoropropene with high purity by flowing the gaseous reaction product through a cooled condenser, trapping and liquefying the gas product in a trap, optionally subjecting the product to deoxidation treatment by water washing and drying treatment etc., and then, subjecting the product to precision distillation.

Unreacted 1-chloro-3,3,3-trifluoropropene can be recovered after the distillation and used again as the raw material. Further, excessively hydrogenated products such as 1,1,1-trifluoropropane can be converted to 3,3,3-trifluoropropene by halogenation or dehydrohalogenation with the use of chlorine etc.

Hydrogen chloride generated as a by-product can be recovered as hydrochloric acid by absorbing the hydrogen chloride into water and separating and removing a slight amount of organic substance, hydrogen fluoride etc. from the resulting solution with the use of an adsorbent.

In the present invention, the reaction system can be selected among a continuous system, a semi-continuous system and a batch system by any skilled in the art.

EXAMPLES

The present invention will be described in more detail below by way of the following examples. It should be noted that the following examples are not intended to limit the present invention thereto. Herein, the unit "%" of each composition analysis value means the area percentage "area %" of an individual component as directly determined by gas chromatography of a reaction mixture. (Unless otherwise specified, a FID was used as a detector in the gas chromatography.)

Preparation Example 1

Preparation of Nickel/Activated Carbon Catalyst

Into a 300-ml eggplant-shaped flask, 40 g of activated carbon (Diasorp G4-8 manufactured by Mitsubishi Chemical Calgon Co., Ltd.) was weighed out accurately. Then, 100 g of 24% hydrochloric acid dissolving therein 1.8 g of nickel chloride was dropped onto the activated carbon. The activated carbon was left still in the hydrochloric acid for 2 days. The thus-obtained metal-impregnated activated carbon was dried under reduced pressure by an evaporator. The oil bath temperature was gradually raised to 150° C. or higher, thereby removing water from the metal-impregnated activated carbon.

Preparation Example 2

Preparation of Palladium/Activated Carbon Catalyst

Into a 500-ml eggplant-shaped flask, 100 g of activated carbon (Granular Shirasagi G2X: 4/6-1 manufactured by Japan EnviroChemicals Ltd.) was weighed out accurately. The activated carbon was then subjected to nitric acid treatment by adding about 150 ml of an aqueous solution containing approximately 20% nitric acid to the activated carbon and leaving the activated carbon in the aqueous nitric acid solution for about 3 hours. Further, a palladium (II) chloride hydrochloric acid solution was prepared by dissolving 0.834 g of palladium (II) chloride in 50 g of 24% hydrochloric acid. The prepared palladium chloride solution was dropped onto the nitric acid-treated activated carbon. The nitric acid-treated activated carbon was left still in the palladium chloride solution for 2 days. The thus-obtained metal-impregnated activated carbon was dried under reduced pressure by an evaporator. The oil bath temperature was gradually raised to 150° C. or higher, thereby removing water from the metal-impregnated activated carbon.

Preparation Example 3

Preparation of Palladium-Bismuth/Activated Carbon Catalyst

Into a 500-ml eggplant-shaped flask, 100 g of activated carbon (Granular Shirasagi G2X: 4/6-1 manufactured by Japan EnviroChemicals Ltd.) was weighed out accurately. The activated carbon was then subjected to nitric acid treatment by adding about 150 ml of an aqueous solution containing approximately 20% nitric acid to the activated carbon and leaving the activated carbon in the aqueous nitric acid solution for about 3 hours. On the other hand, 1.160 g of bismuth (III) nitrate pentahydrate and 200 ml of an aqueous solution containing approximately 30% nitric acid were mixed together in a 300-ml beaker. The beaker was heated in a hot water bath to completely dissolve the bismuth nitrate pentahydrate in the aqueous nitric acid solution. Further, a palladium (II) chloride hydrochloric acid solution was prepared by dissolving 0.834 g of palladium (II) chloride in 50 g of 24% hydrochloric acid, and then, mixed with the above-prepared bismuth nitrate solution. The mixed solution was dropped onto the nitric acid-treated activated carbon. The nitric acid-treated activated carbon was left still in the mixed solution for 2 days. The thus-obtained metal-impregnated activated carbon was dried under reduced pressure by an evaporator. The oil bath temperature was gradually raised to 150° C. or higher, thereby removing water from the metal-impregnated activated carbon.

Example 1

Into a reactor of SUS316L having an inside diameter of 20 mm and a length of 30 cm, 40 ml of Ru/activated carbon catalyst (Ru content: 0.5 mass %) manufactured by N.E. Chemcat Corporation was packed as the catalyst A. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml/min through the reactor, the temperature of the reactor was raised by 30° C. up to 300° C. The temperature of the reactor was subsequently lowered to 170° C. while flowing hydrogen through the reactor. In this state, 1-chloro-3,3,3-trifluoropropene was introduced into the reactor. After a lapse of about 1 hour, the resulting product gas was sampled and analyzed by gas chromatography. The conversion rate of 1-chloro-3,3,3-trifluoropropene was 69.7%; and the selectivity of 3,3,3-trifluoropropene was 41.0%.

Example 2

Into a reactor of SUS316L having an inside diameter of 20 mm and a length of 30 cm, 40 ml of hopcalite catalyst (CuO—MnO; KCG manufactured by Süd-Chemie Catalysts Inc.) was packed as the catalyst B. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml/min through the reactor, the temperature of the reactor was raised by 30° C. up to 300° C. The temperature of the reactor was subsequently lowered to 200° C. while flowing hydrogen at a flow rate of 75 ml/min through the reactor. In this state, 1-chloro-3,3,3-trifluoropropene was introduced into the reactor. After a lapse of about 1 hour, the resulting product gas was sampled and analyzed by gas chromatography. The conversion rate of 1-chloro-3,3,3-trifluoropropene was 14.1%; the selectivity of 3,3,3-trifluoropropene was 93.6%; and the selectivity of 3,3,3-trifluoropropane was 2.5%.

Example 3

In a reactor of SUS316L having an inside diameter of 20 mm and a length of 30 cm, 40 ml of hopcalite catalyst (CuO—MnO; KCG manufactured by Süd-Chemie Catalysts Inc.) was packed and treated in the same manner as in Example 2. After the treatment, the temperature of the reactor was set to 290° C. while flowing hydrogen at a flow rate of 75 ml/min through the reactor. In this state, 1-chloro-3,3,3-trifluoropropene was introduced into the reactor. After a lapse of about 1 hour, the resulting product gas was sampled and analyzed by gas chromatography. The conversion rate of 1-chloro-3,3,3-trifluoropropene was 71.6%; the selectivity of 3,3,3-trifluoropropene was 94.7%; and the selectivity of 3,3,3-trifluoropropane was 2.2%.

Example 4

Into a reactor of SUS316L having an inside diameter of 20 mm and a length of 30 cm, 40 ml of the nickel/activated catalyst prepared in Preparation Example 1 was packed as the catalyst A. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml/min through the reactor, the temperature of the reactor was raised by 30° C. up to 300° C. The temperature of the reactor was subsequently lowered to 280° C. while flowing hydrogen through the reactor. In this state, 1-chloro-3,3,3-trifluoropropene was introduced into the reactor. The reaction was stabilized after a lapse of about 1 hour. The resulting product gas was sampled and analyzed by gas chromatography. The conversion rate of 1-chloro-3,3,3-trifluoropropene was 8.0%; the selectivity of 3,3,3-trifluoropropene was 40.2%; and the selectivity of 3,3,3-trifluoropropane was 3.0%.

Example 5

Into a reactor of SUS316L having an inside diameter of 20 mm and a length of 30 cm, 40 ml of the palladium-bismuth/activated catalyst prepared in Preparation Example 3 was packed as the catalyst C. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml/min through the reactor, the temperature of the reactor was raised by 30° C. up to 300° C. The temperature of the reactor was subsequently lowered to 200° C. while flowing hydrogen through the reactor. In this state, 1-chloro-3,3,3-trifluoropropene was introduced into the reactor. After a lapse of about 1 hour, the resulting product gas was sampled and analyzed by gas chromatography. The conversion rate of 1-chloro-3,3,3-trifluoropropene was 78.9%; and the selectivity of 3,3,3-trifluoropropene was 88.7%.

Comparative Example 1

Into a reactor of SUS316L having an inside diameter of 20 mm and a length of 30 cm, 40 ml of Pt/activated carbon catalyst (Pt content: 0.5 mass %) manufactured by N.E. Chemcat Corporation was packed. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 220° C. While flowing nitrogen at a flow rate of 10 ml/min and flowing hydrogen at a flow rate of 30 ml/min through the reactor, the temperature of the reactor was raised by 30° C. up to 300° C. Subsequently, 1-chloro-3,3,3-trifluoropropene was introduced into the reactor at 220° C. while flowing hydrogen through the reactor. After a lapse of about 1 hour, the resulting product gas was subjected to composition analysis. The conversion rate of 1-chloro-3,3,3-trifluoropropene was 99.8%; the selectivity of 3,3,3-trifluoropropene was 0.1%; and the selectivity of 3,3,3-trifluoropropane was 99.5%.

Comparative Example 2

Into a reactor of SUS316L having an inside diameter of 20 mm and a length of 30 cm, 40 ml of Re/activated carbon catalyst (Re content: 0.5 mass %) manufactured by N.E. Chemcat Corporation was packed. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 210° C. While flowing nitrogen at a flow rate of 10 ml/min and flowing hydrogen at a flow rate of 30 ml/min through the reactor, the temperature of the reactor was raised by 30° C. up to 300° C. The temperature of the reactor was subsequently lowered to 210° C. while flowing hydrogen at a flow rate of 75 ml/min through the reactor. In this state, 1-chloro-3,3,3-trifluoropropene was introduced into the reactor. After a lapse of about 1 hour, the resulting product gas was subjected to composition analysis. The conversion rate of 1-chloro-3,3,3-trifluoropropene was 14.3%; the selectivity of 3,3,3-trifluoropropene was 3.7%; and the selectivity of 3,3,3-trifluoropropane was 94.6%.

Comparative Example 3

Into a reactor of SUS316L having an inside diameter of 20 mm and a length of 30 cm, 40 ml of the catalyst prepared in Preparation Example 2 was packed. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml/min through the reactor, the temperature of the reactor was raised by 30° C. up to 300° C. The temperature of the reactor was subsequently lowered to 200° C. while flowing hydrogen through the reactor. In this state, 1-chloro-3,3,3-trifluoropropene was introduced into the reactor. After a lapse of about 1 hour, the resulting product gas was sampled and analyzed by gas chromatography. The conversion rate of 1-chloro-3,3,3-trifluoropropene was 96.0%; and the selectivity of 3,3,3-trifluoropropene was 2.5%.

The results of the above examples and comparative examples are summarized in TABLE 1.

TABLE 1

| Catalyst | | Mol ratio ($H_2$/1233zd) | $H_2$ (ml/min) | Raw material feeding rate (g/min) |
|---|---|---|---|---|
| Example 1 | 0.5%Ru/C | 2 | 30 | 0.1 |
| Example 2 | Hopcalite KCG-1 (Cu—Mn) | 4 | 75 | 0.15 |
| Example 3 | Hopcalite KCG-1 (Cu—Mn) | 4 | 75 | 0.15 |
| Example 4 | 2%Ni/C | 2 | 30 | 0.1 |
| Example 5 | 0.5%Bi—0.5%Pd/C | 2 | 30 | 0.1 |
| Comparative Example 1 | 0.5%Pt/C | 2 | 30 | 0.1 |
| Comparative Example 2 | 0.5%Re/C | 4 | 75 | 0.11 |
| Comparative Example 3 | 0.5%Pd/C | 2 | 30 | 0.1 |

| | Reaction temperature (° C.) | Raw material conversion rate (%) | TFPe selectivity (%) | TFP selectivity (%) |
|---|---|---|---|---|
| Example 1 | 170 | 69.7 | 41.0 | 54.2 |
| Example 2 | 200 | 14.1 | 93.6 | 2.5 |
| Example 3 | 290 | 71.6 | 94.7 | 2.2 |
| Example 4 | 280 | 8.0 | 40.2 | 3.0 |
| Example 5 | 200 | 78.9 | 88.7 | 3.6 |
| Comparative Example 1 | 220 | 99.8 | 0.1 | 99.5 |
| Comparative Example 2 | 210 | 14.3 | 3.7 | 94.6 |
| Comparative Example 3 | 200 | 96.0 | 2.5 | 97.0 |

TFPe: 3,3,3-trifluoropropene
TFP: 3,3,3-trifluoropropane
Reactor: ID 200 mmφ × 300 mm
Heating means: electric heater
Catalyst amount: 40 ml As is apparent from TABLE 1, 3,3,3-trifluoropropene was obtained with high selectivity by gas-phase hydrogenation of 1-chloro-3,3,3-trifluoropropene with hydrogen ($H_2$) in the presence of either one of the catalysts A, B and C of the present invention.

As described above, it is possible according to the present invention to produce 3,3,3-trifluoropropene efficiently on an industrial scale. The reaction of the present invention is not at all disclosed in any relevant technical fields and is a superior production method because the reaction proceeds with very high selectivity and has an advantage in production that the starting material can be industrially easily prepared.

Although the present invention has been described with reference to the above embodiments, various modifications and variations of the above embodiments can be made based on the knowledge of those skilled in the art without departing from the scope of the present invention.

The invention claimed is:
1. A method for producing 3,3,3-trifluoropropene, comprising:
performing hydrogenation of 1-chloro-3,3,3-trifluoropropene with hydrogen ($H_2$) in gas phase in the presence of either: (A) a catalyst having ruthenium carried on activated carbon; or (B) an oxide catalyst of copper and manganese.

2. The method for producing 3,3,3-trifluoropropene according to claim 1, wherein the amount of the ruthenium is 0.1 to 20 mass % based on the amount of the activated carbon.

3. The method for producing 3,3,3-trifluoropropene according to claim 1, wherein the hydrogenation is performed at a temperature of 150 to 300° C.

4. The method for producing 3,3,3-trifluoropropene according to claim 1, wherein the amount of the hydrogen used is 1 to 5 mol per 1 mol of the 1-chloro-3,3,3-trifluoropropene.

5. The method for producing 3,3,3-trifluoropropene according to claim 1, further comprising: recovering and returning unreacted 1-chloro-3,3,3-trifluoropropene to the hydrogenation step.

6. The method for producing 3,3,3-trifluoropropene according to claim 1, wherein the oxide catalyst (B) is a catalyst containing oxides of copper and manganese as main components.

7. The method for producing 3,3,3-trifluoropropene according to claim 1, wherein the oxide catalyst (B) is a hopcalite catalyst.

* * * * *